US006368281B1

(12) United States Patent
Solomon et al.

(10) Patent No.: US 6,368,281 B1
(45) Date of Patent: Apr. 9, 2002

(54) TWO-DIMENSIONAL PHASED ARRAY ULTRASOUND TRANSDUCER WITH A CONVEX ENVIRONMENTAL BARRIER

(76) Inventors: Rodney J Solomon, 25 Gavin Cir., Andover, MA (US) 01810; Benjamin M Herrick, 94 Waite Rd., Boxborough, MA (US) 01719

( * ) Notice: Subject to any disclaimer, the term of this patent is extended or adjusted under 35 U.S.C. 154(b) by 0 days.

(21) Appl. No.: 09/365,303

(22) Filed: Jul. 30, 1999

(51) Int. Cl.[7] .................................................. A61B 8/14
(52) U.S. Cl. ...................................................... 600/459
(58) Field of Search ................................ 600/437, 459, 600/443; 310/322, 323–326; 367/153; 73/642, 644, 626

(56) References Cited

U.S. PATENT DOCUMENTS

| | | | | |
|---|---|---|---|---|
| 4,211,949 A | * | 7/1980 | Brisken et al. | 310/322 |
| 4,441,503 A | * | 4/1984 | O'Donnell | 600/437 |
| 4,641,660 A | * | 2/1987 | Bele | 600/437 |
| 4,867,169 A | * | 9/1989 | Machida et al. | 600/459 |
| 5,027,659 A | * | 7/1991 | Bele et al. | 73/626 |
| 5,099,459 A | * | 3/1992 | Smith | 367/153 |
| 5,426,980 A | * | 6/1995 | Smith | 73/644 |
| 6,102,860 A | * | 8/2000 | Mooney | 600/443 |
| 6,120,452 A | * | 9/2000 | Barthe et al. | 600/459 |

OTHER PUBLICATIONS

"Linear Arrays: Theory of Operation and Performance", Aero–Tech Report. vol. 20, 1, Krautkramer–Branson, Inc., 1981.

* cited by examiner

*Primary Examiner*—Marvin M. Lateef
*Assistant Examiner*—Ali M. Imam
(74) *Attorney, Agent, or Firm*—John F. Volopia

(57) ABSTRACT

A two-dimensional phased array ultrasound transducer comprises a transducer housing, a sensor mounted within the housing, and a convex environmental barrier for placement against, and maximizing contact with, a patient's body. The environmental barrier does not necessarily provide any focusing capability, therefore the propagation velocity of sound through the environmental barrier is approximately equal to the propagation velocity of sound through tissue of the patient's body.

7 Claims, 5 Drawing Sheets

420
422
415
405
408
410

TWO-DIMENSIONAL PHASED ARRAY ULTRASOUND TRANSDUCER 305
RIB CAGE 310
INTERNAL ORGAN 315
CONVEX BARRIER 320
325
330

TWO-DIMENSIONAL PHASED ARRAY ULTRASOUND TRANSDUCER WITH A CONVEX ENVIRONMENTAL BARRIER

FIELD OF THE INVENTION

The present invention relates to two-dimensional phased array ultrasound transducers and, more particularly, to a two-dimensional phased array ultrasound transducer with a convex environmental barrier for maximizing contact with a patient's body.

BACKGROUND OF THE INVENTION

Ultrasound systems offer a non-invasive means for medical personnel to monitor physiological activity within a patient's body. Such a system includes an ultrasound transducer that is positioned against the patient's body. The transducer transmits ultrasonic signals into the patient's body, and receives echo signals that are then processed to provide an image of an internal organ. An acoustic gel is placed between the transducer and the patient's body to improve acoustic coupling of the ultrasonic signals.

Ultrasound transducers are categorized as either one-dimensional phased arrays or two-dimensional phased arrays. These two categories of transducers are fundamentally different in terms of their functional and structural requirements.

One-dimensional phased array ultrasound transducers have been used in the field of medical imaging for several decades. A typical one-dimensional transducer is a flat, rectangular plate measuring approximately 12 mm×20 mm and holds a linear array of, for example, 64 piezoelectric elements set adjacent to one another. An ultrasound beam produced by the transducer is electronically focused in only an azimuth plane, and must be focused in an elevation plane by use of a lens.

In order to achieve the desired focus, the typical one-dimensional transducer uses a soft acoustic convex lens. Such a lens is made of a material that propagates sound at a slower velocity than that through the tissue of the patient, to achieve the focusing effect.

Two-dimensional phased array transducers are relatively new to the field of medical imaging. A typical two-dimensional transducer is configured with a flat array of piezoelectric elements in an x-y matrix. For example, an array of 3000 elements can be arranged in a matrix of 50×60 elements. An ultrasound beam produced by such a transducer is electronically steered and focused in both an azimuth plane and an elevation plane. In contrast with the one-dimensional transducer, the two-dimensional transducer does not require a lens for focusing the ultrasound beam.

FIG. 1 illustrates a partial two-dimensional phased array ultrasound transducer according to the prior art. A lead zirconate titanate (PZT) sensor 115 is mounted on a sensor support structure 110, which is enclosed within a transducer housing 105. Although this transducer does not require a lens for focusing, an environmental barrier (not shown) must be positioned on sensor 115 to prevent exposure of the sensor elements to acoustic gel and other environmental contaminants such as sterilants. The barrier also serves to protect a clinician and patient from electrical hazards caused by applied voltage to the transducer elements.

FIG. 2 illustrates an application of a prior art two-dimensional phased array ultrasound transducer. A two-dimensional phased array ultrasound transducer 205 includes a barrier 225. Transducer 205 transmits an ultrasonic signal through a patient's rib cage 215, and receives and processes echo signals in order to produce an image of internal organ 220.

Since barrier 225 is not used for focusing, it is flat and has a uniform thickness. This construction introduces a problem. As transducer 205 is repositioned on the patient's body 235, in an effort to obtain an optimum image of internal organ 220, the acoustic gel (not shown) that is used during the ultrasound procedure is forced out from between barrier 225 and the patient's skin 230. An air gap 210 forms between barrier 225 and the patient's skin 230. Ultrasound signals do not propagate well through air. Consequently, the desired image of internal organ 220 is not obtained.

Accordingly, there is a need for a two-dimensional phased array ultrasound transducer with an improved environmental barrier for maximizing contact with a patient's body.

SUMMARY OF THE INVENTION

A two-dimensional phased array ultrasound transducer incorporating the present invention comprises a transducer housing, a sensor mounted within the housing, and a convex environmental barrier for placement against, and for maximizing contact with, a patient's body. The environmental barrier does not necessarily provide any focusing capability, therefore the propagation velocity of sound through the environmental barrier is approximately equal to the propagation velocity of sound through tissue of the patient's body.

The barrier can be manufactured of a material such as polyurethane, low-density polyethylene or a thermoplastic elastomer. Its contour can be a portion of an elliptical, parabolic, cylindrical or spherical surface.

The present invention reduces the opportunity for an air gap to develop between the environmental barrier and the patient's body. Accordingly, the quality of an ultrasound image is improved.

DETAILED DESCRIPTION OF THE PREFERRED EMBODIMENT

Figure 1:
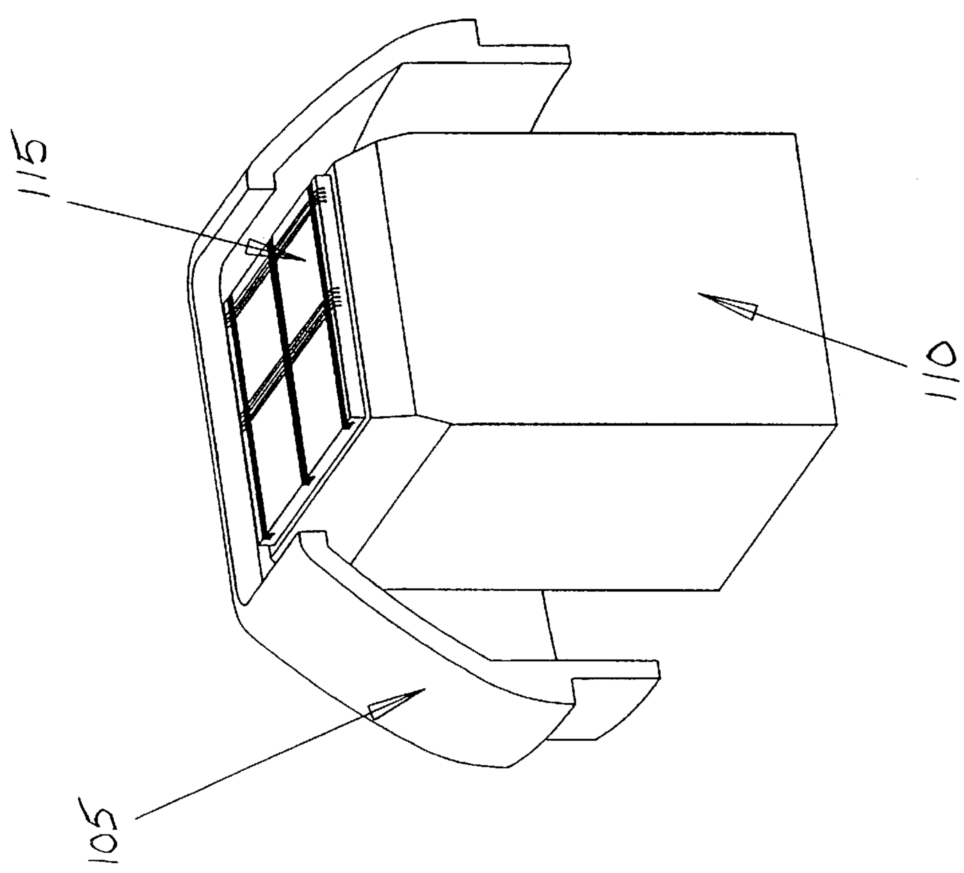
FIG. 1 is a front perspective view of a partial two-dimensional phased array ultrasound transducer according to the prior art.
Figure 2:
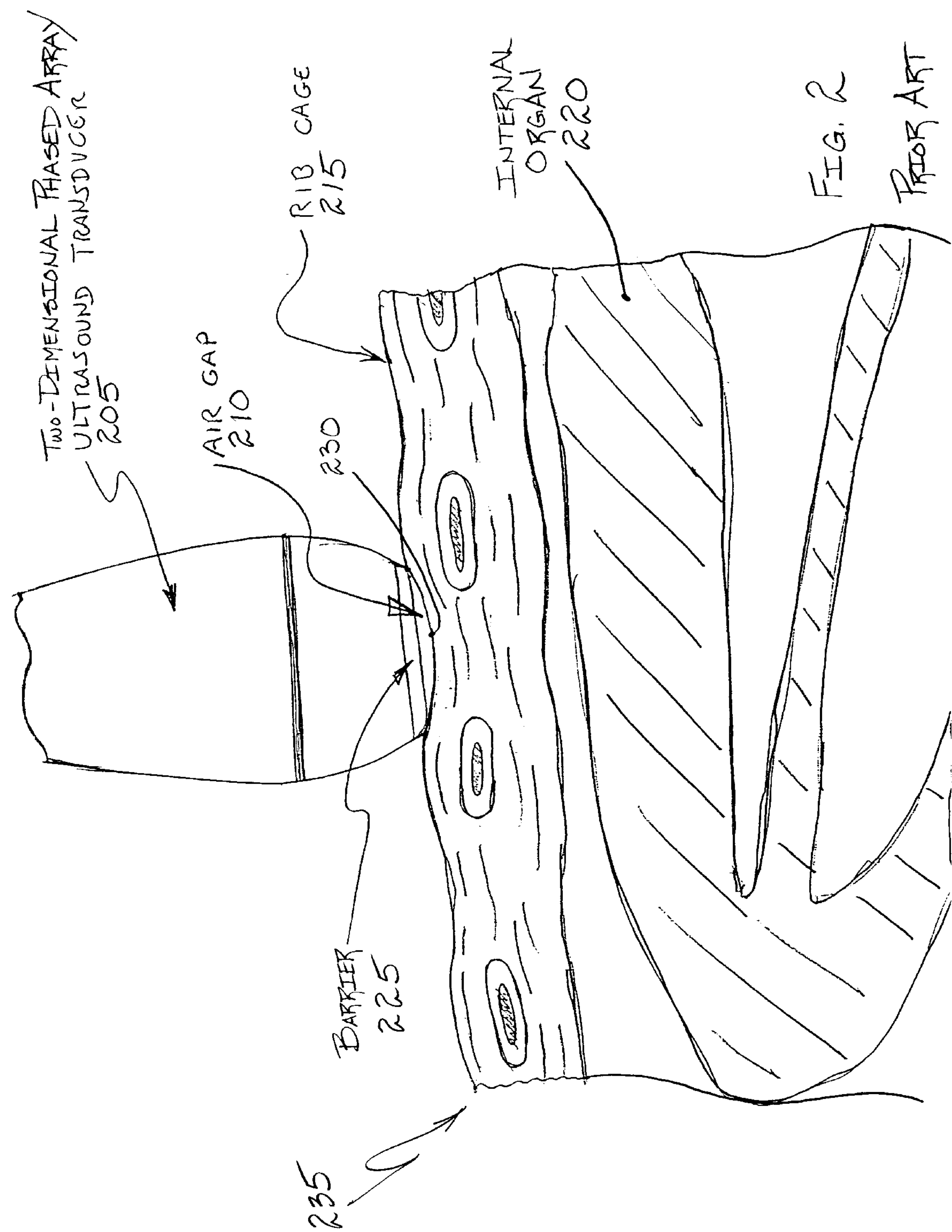
FIG. 2 is a front view of a two-dimensional phased array ultrasound transducer according to the prior art, in use with portions broken away, shown partially in elevation and partially in vertical section.
Figure 3:
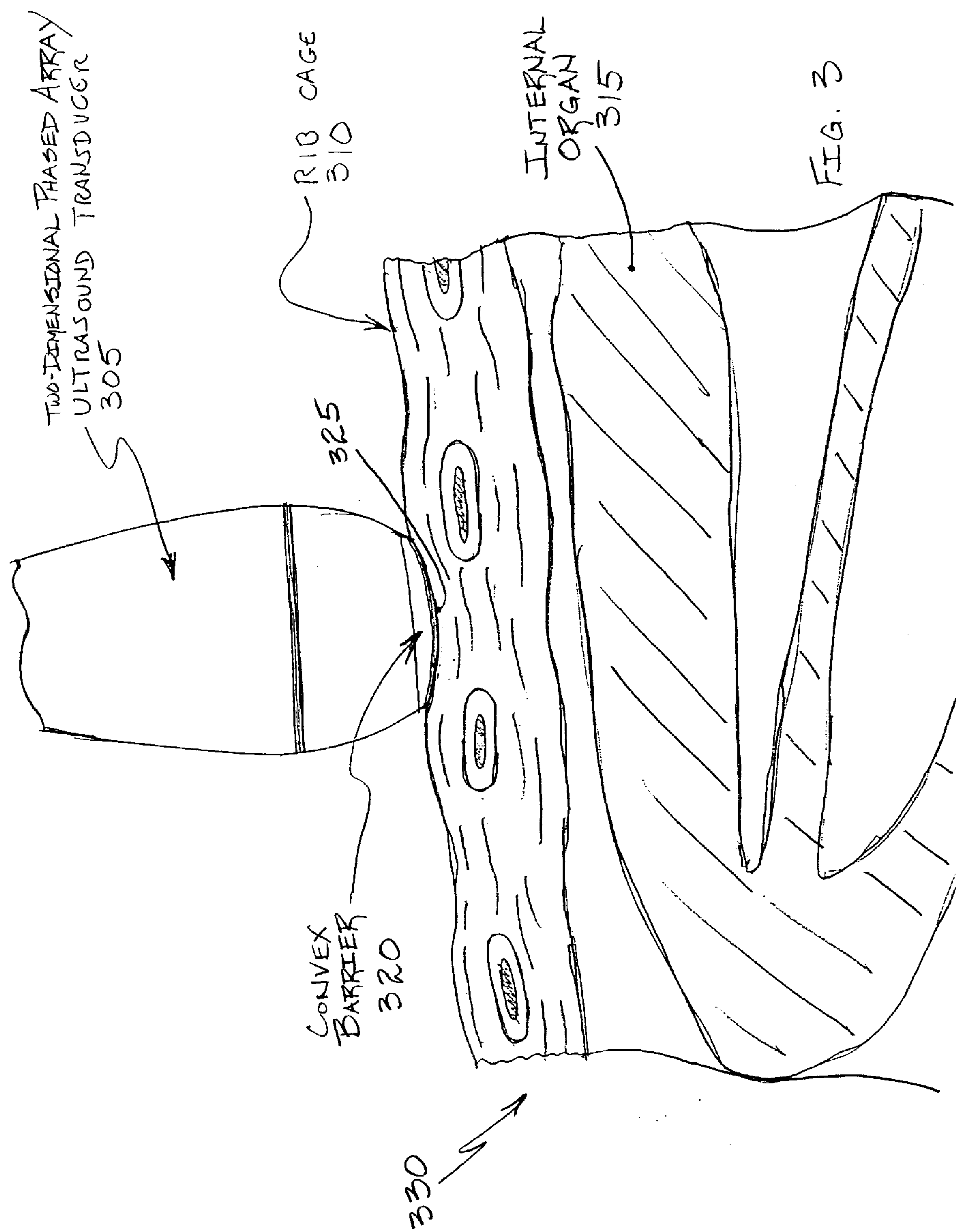
FIG. 3 is a front view of a two-dimensional phased array ultrasound transducer according to the present invention, in use with portions broken away, shown partially in elevation and partially in vertical section.

FIG. 3 illustrates an application of a two-dimensional phased array ultrasound transducer according to the present invention. Two-dimensional phased array ultrasound transducer 305 has a convex barrier 320 for maximizing contact with a patient's body 330. For example, when ultrasound transducer 305 is placed against a rib cage 310, the patient's skin 325 readily conforms to the shape of convex barrier 320. The possibility of forming an air gap between convex barrier 320 and the patient's skin 325 is greatly reduced and the quality of an image of an internal organ 315 is improved.

Two-dimensional phased array ultrasound transducer 305 electronically steers and focuses an ultrasound beam. Therefore, convex barrier 320 need not function as a lens for the purpose of focusing the beam. Since focusing is not an issue, the propagation velocity of sound through convex barrier 320 can be either less than or greater than the propagation velocity of sound through tissue in the patient's body. More particularly, it need not be less than the propagation velocity of sound through tissue in the patient's body, as required for a convex lens used for focusing.

Most preferably, convex barrier 320 is manufactured of a material having a propagation velocity of sound approximately equal to the propagation velocity of sound through tissue in the patient's body. Any mismatch that occurs can be compensated electronically. The propagation velocity of sound in a human body is approximately 1.5 millimeters/microsecond (mm/μs). Convex barrier 320 can be manufactured of materials such as Dynaflex 2970, a styrenic block copolymer from GLS Corporation, of McHenry, Ill., with a sound speed of 1.52 mm/μs; Santoprene 101-64, a polypropylene/EPDM alloy from Advanced Elastomer Systems, of Akron, Ohio, with a sound speed of 1.51 mm/μs; or Pebax 25335N-00, a polyether block amide from Elf Atochem, of Paris, France, with a sound speed of 1.55 mm/μs.

Figure 4:
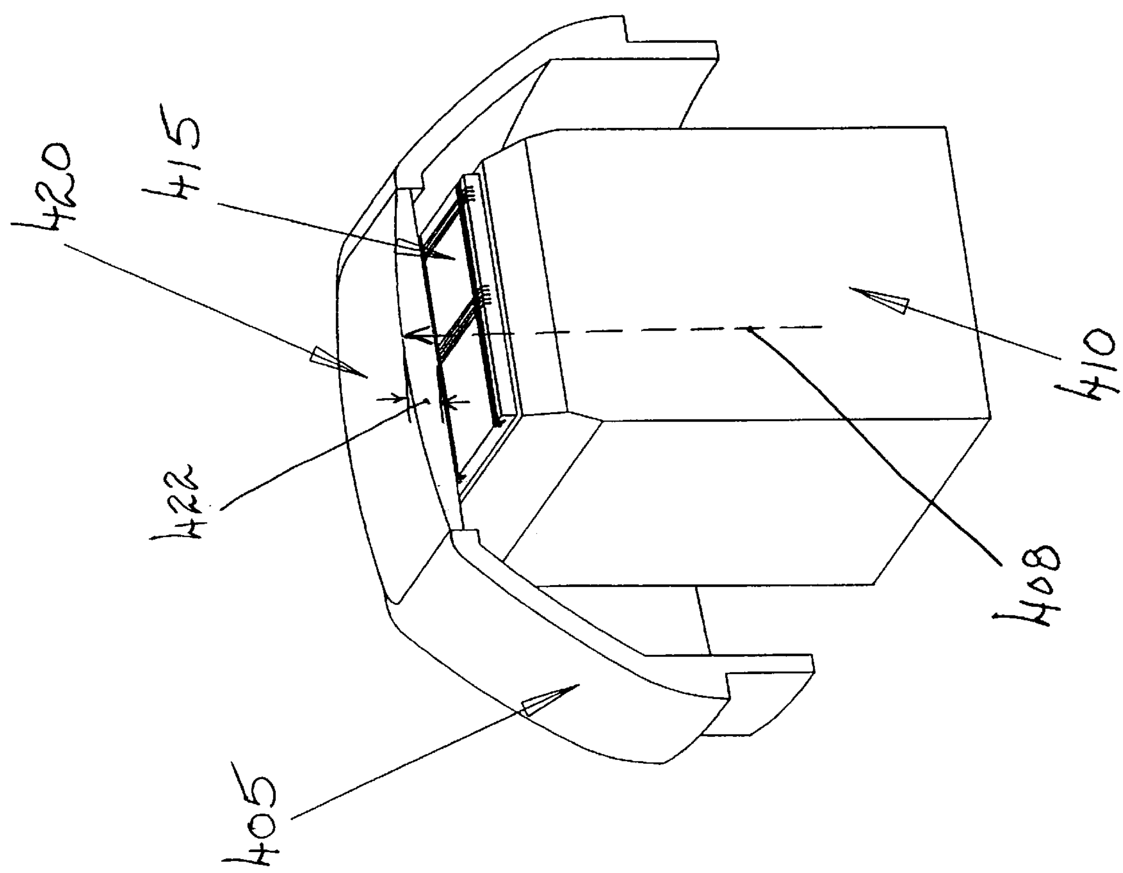
FIG. 4 is a front perspective view of one embodiment of a two-dimensional phased array ultrasound transducer according to the present invention.

FIG. 4 shows a cut-away view of one embodiment of a two-dimensional phased array ultrasound transducer according to the present invention. A PZT sensor 415 is mounted on a sensor support structure 410, which is enclosed within a transducer housing 405. An environmental barrier 420 positioned adjacent to sensor 415 is a portion of a cylindrical surface having a radius of curvature 408 of approximately 2 to 5 centimeters. Environmental barrier 420 has a center thickness 422 of approximately 0.75 to 1.0 millimeters.

Figure 5:
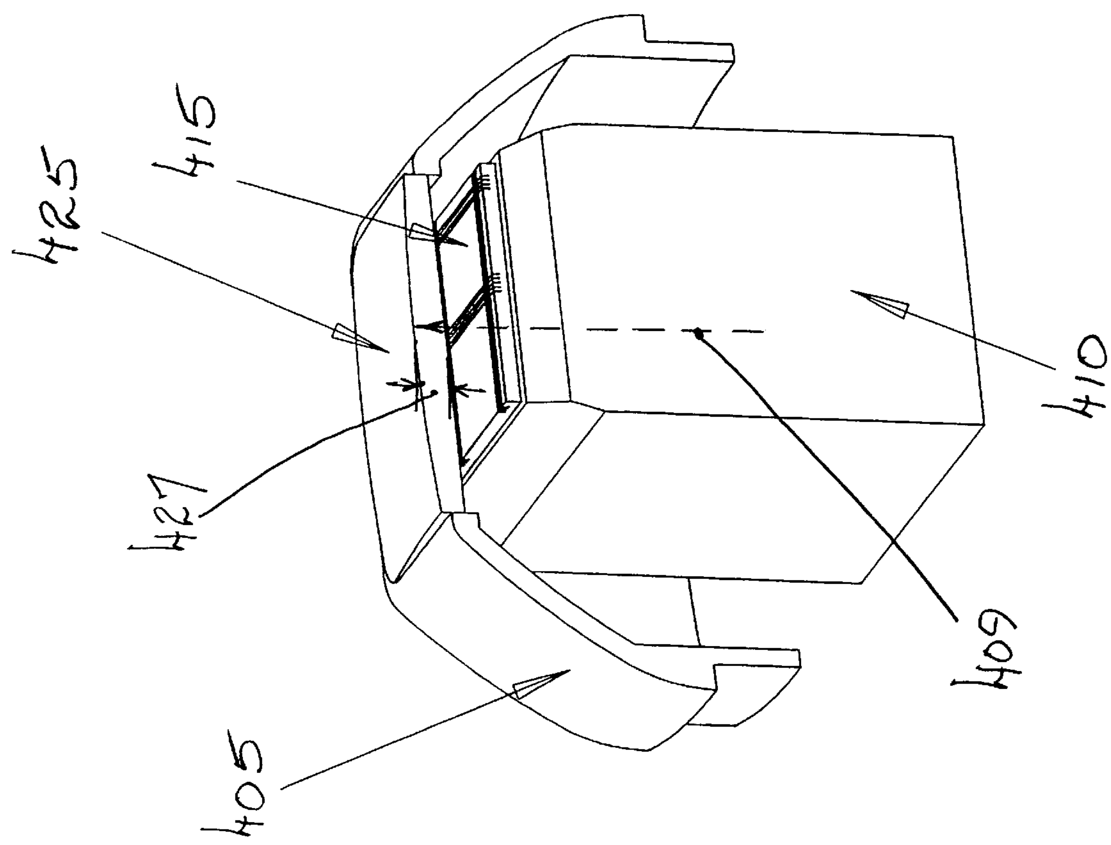
FIG. 5 is a front perspective view of a second embodiment of a two-dimensional phased array ultrasound transducer according to the present invention.

FIG. 5 shows a cut-away view of a second embodiment of a two-dimensional phased array ultrasound transducer according to the present invention. A lead zirconate titanate (PZT) sensor 415 is mounted on a sensor support structure 410, which is enclosed within a transducer housing 405. An environmental barrier 425 positioned adjacent to sensor 415 is a portion of a spherical surface having a radius of curvature 409 of approximately 2 to 5 centimeters. Environmental barrier 425 has a center thickness 427 of approximately 0.75 to 1.0 millimeters.

It should be understood that the foregoing description is only illustrative of the invention. Various alternatives and modifications can be devised by those skilled in the art without departing from the invention. Accordingly, the present invention is intended to embrace all such alternatives, modifications and variances that fall within the scope of the appended claims.

What is claimed is:

1. An ultrasound transducer comprising:

a transducer housing;

a two-dimensional phased array sensor mounted within said transducer housing; and a barrier having a first surface adjacent to said sensor, and a second surface opposite said first surface for placement against a patient's body, said second surface having a convex contour for maximizing contact with said patient's body;

said barrier having a propagation velocity of sound that is approximately equal to a propagation velocity of sound through tissue of said patient's body.

2. The ultrasound transducer recited in claim 1, wherein said propagation velocity of sound through said barrier is approximately 1.5 millimeters/microsecond.

3. The ultrasound transducer recited in claim 1, wherein said barrier is made of a material selected from the group consisting of polyurethane, low-density polyethylene and thermoplastic elastomer.

4. The ultrasound transducer recited in claim 1, wherein said second surface is a portion of a cylindrical surface.

5. The ultrasound transducer recited in claim 1, wherein said second surface is a portion of a spherical surface.

6. The ultrasound transducer recited in claim 1, wherein said convex contour has a radius of curvature of approximately 2 to 5 centimeters.

7.The ultrasound transducer recited in claim 1, wherein said barrier has a center thickness of approximately 0.75 to 1.0 millimeters.

* * * * *